United States Patent [19]

Holmwood et al.

[11] Patent Number: 4,584,373
[45] Date of Patent: * Apr. 22, 1986

[54] 1-(SUBSTITUTED-PHENOXY)-3-METHYL-2-(PYRIMIDIN-5-YL)-BUTAN-2-OL USEFUL AS PLANT GROWTH REGULATING AGENTS

[75] Inventors: Graham Holmwood, Wuppertal; Klaus Lürssen, Bergisch-Gladbach; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[ * ] Notice: The portion of the term of this patent subsequent to May 21, 2002 has been disclaimed.

[21] Appl. No.: 626,814

[22] Filed: Jul. 2, 1984

[30] Foreign Application Priority Data

Jul. 16, 1983 [DE] Fed. Rep. of Germany ....... 3325761

[51] Int. Cl.$^4$ .................... C07D 239/02; A01N 43/50
[52] U.S. Cl. .................... 544/225; 544/335; 514/256; 71/92; 71/97
[58] Field of Search .................... 544/335, 225; 71/92, 71/97; 424/251, 245

[56] References Cited

FOREIGN PATENT DOCUMENTS 0001399 4/1979 European Pat. Off. .
0028755 5/1981 European Pat. Off. .
2742173 3/1979 Fed. Rep. of Germany .
2944850 5/1981 Fed. Rep. of Germany .

OTHER PUBLICATIONS

Holmwood et al., Chem. Abst. 95: 56388m, equiv. Ger. Offen. 2944850.
Holmwood et al., Chem. Abst. 90:204138u, equiv. Ger. Offen. 2742173.
European Search Report and list of equivalents Primary Examiner—Donald G. Daus
Assistant Examiner—Cecilia Shen
Attorney, Agent, or Firm—Sprung Horn Kramer & Woods

[57] ABSTRACT

Combating fungi and/or regulating the growth of plants with novel aroxy-pyrimidinyl-alkanols of the formula

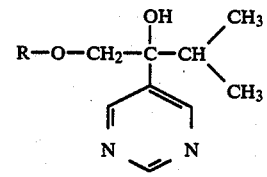

in which R is optionally substituted naphthyl, or

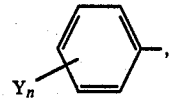

Y each independently is halogen, alkyl, cycloalkyl, alkoxy, halogenoalkyl, halogenoalkoxy, alkylthio, optionally substituted phenyl, optionally substituted phenoxy, optionally substituted phenylalkoxy or optionally substituted phenylalkyl, or addition products thereof with acids or metal salts.

7 Claims, No Drawings

1-(SUBSTITUTED-PHENOXY)-3-METHYL-2-(PYRIMIDIN-5-YL)-BUTAN-2-OL USEFUL AS PLANT GROWTH REGULATING AGENTS

The present invention relates to new aroxy-pyrimidinyl-alkanols, a process for their preparation and their use as plant growth regulators and fungicides.

It has already been disclosed that certain phenoxy-pyrimidinyl-alkanols have plant growth-regulating and fungicidal properties compare DE-OS (German Published Specification) No. 2,742,173 and DE-OS (German Published Specification) No. 2,944,850). Thus, for example, 3,3-dimethyl-1-(4-chloro-phenoxy)-2-(pyrimidin-5-yl)-butan-2-ol can be used for regulating plant growth and for combating fungi. The action of this substance is good, but in some cases leaves something to be desired when low amounts are applied.

New aroxy-pyrimidinyl-alkanols of the formula

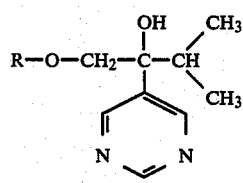

in which R represents optionally substituted naphthyl or the radical of the formula

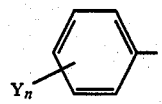

wherein
Y represents halogen, alkyl, cycloalkyl, alkoxy, halogenoalkyl, halogenoalkoxy, alkylthio, optionally substituted phenyl, optionally substituted phenoxy, optionally substituted phenylalkoxy or optionally substituted phenylalkyl and
n represents 0, 1, 2 or 3,
and acid addition salts and metal salt complexes thereof, have now been found.

The aroxy-pyrimidinyl-alkanols contain an asymmetrically substituted carbon atom and can therefore exist in the two optical isomer forms or as racemates. The invention relates both to the isomer mixtures and to the individual isomers.

It has furthermore been found that the aroxy-pyrimidinyl-alkanols of the formula (I) and acid addition salts and metal salt complexes thereof are obtained when aroxy-ketones of the formula

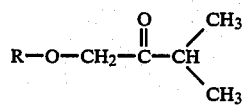

in which R has the abovementioned meaning,
are reacted with pyrimidinyl halides of the formula

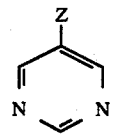

in which Z represents halogen,
in the presence of a diluent and in the presence of an alkali metal-organic compound, and, if appropriate, an acid or a metal salt is then added on.

Finally, it has been found that the new aroxy-pyrimidinyl-alkanols of the formula (I) have very good plant growth-regulating and fungicidal properties.

It is to be described as exceptionally surprising that the aroxy-pyrimidinyl-alkanols of the formula (I) according to the invention have a better plant growth-regulating and fungicidal action than 3,3-dimethyl-1-(4-chloro-phenoxy)-2-(pyrimidin-5-yl)-butan-2-ol which is structurally the most similar active compound of the same type of action, which is already known.

Formula (I) provides a general definition of the aroxy-pyrimidinyl-alkanols according to the invention. In this formula, R preferably represents naphthyl which is optionally substituted by halogen, or represents the radical of the formula

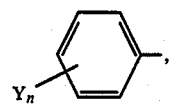

wherein
Y preferably represents fluorine, chlorine, bromine, alkyl with 1 to 4 carbon atoms, cycloalkyl with 5 to 7 carbon atoms, alkoxy with 1 to 4 carbon atoms, halogenoalkyl with up to 2 carbon atoms and 1 to 5 halogen atoms, halogenoalkoxy with 1 or 2 carbon atoms and 1 to 5 halogen atoms, alkylthio with 1 to 4 carbon atoms, phenyl which is optionally substituted by halogen and/or alkyl with 1 to 4 carbon atoms, phenoxy which is optionally substituted by halogen and/or alkyl with 1 to 4 carbon atoms, phenylalkoxy which has 1 to 4 carbon atoms in the alkoxy part and is optionally substituted by halogen and/or alkyl with 1 to 4 carbon atoms, or phenylalkyl which has 1 to 4 carbon atoms in the alkyl part and is optionally substituted by halogen and/or alkyl with 1 to 4 carbon atoms, and
the index n represents 0, 1, 2 or 3,
and wherein the substituents designated by the symbol Y can be identical or different.

Particularly preferred compounds of the formula (I) are those
in which R represents naphth-1-yl which is optionally substituted by fluorine, chlorine and/or bromine, or represents the radical of the formula

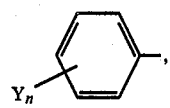

wherein
Y represents fluorine, chlorine, bromine, methyl, ethyl, isopropyl, n-propyl, cyclohexyl, methoxy, ethoxy, n-propoxy, isopropoxy, halogenoalkyl with 1 or 2 carbon atoms and 1 to 3 fluorine and/or chlorine atoms, halogenoalkoxy with 1 or 2 carbon atoms and 1 to 3 fluorine and/or chlorine atoms, methylthio, ethylthio, phenyl which is optionally substituted by fluorine, chlorine, methyl and/or ethyl, phenoxy which is optionally substituted by fluorine, chlorine, methyl and/or ethyl, phenylalkyl which has 1 or 2 carbon atoms in the alkylene group and is optionally substituted by fluorine, chlorine, methyl and/or ethyl, or phenylalkoxy which has 1 or 2 carbon atoms in the alkoxy group and is optionally substituted by fluorine, chlorine, methyl and/or ethyl, and the index n represents 0, 1, 2 or 3.

Acid addition salts of aroxy-pyrimidinyl-alkanols of the formula (I) in which R has the abovementioned preferred meanings are also preferred substances according to the invention. Those salts which are formed by addition from the following acids are particularly preferred here: hydrochloric acid, hydrobromic acid, phosphoric acid, nitric acid, sulphuric acid, p-toluenesulphonic acid or 1,5-naphthalene-disulphonic acid.

Metal salt complexes of aroxy-pyrimidinyl-alkanols of the formula (I) in which R has the abovementioned preferred meanings are also preferred substances according to the invention. Those complexes which contain salts of metals of main groups II to IV and of subgroups I and III and IV to VIII of the periodic system are particularly preferred here, examples of metals which may be mentioned being copper, zinc, manganese, magnesium, tin, iron and nickel.

If 1-(4-chloro-phenoxy)-3-methyl-butan-2-one and 5-bromo-pyrimidine are used as starting substances and n-butyl-lithium is used as the alkali metal-organic compound, the course of the process according to the invention can be represented by the following equation:

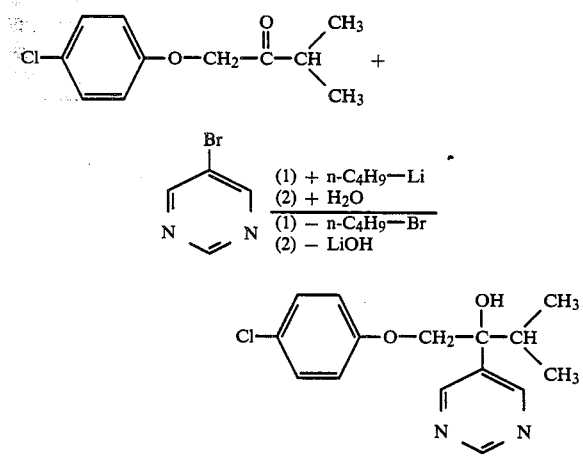

Formula (II) provides a general definition of the aroxy-ketones required as starting substances in the process according to the invention. In this formula, R preferably represents those radicals which have already been mentioned as preferred for these substituents in connection with the description of the substances of the formula (I) according to the invention.

Aroxy-ketones of the formula (II) are known, and they can be prepared in a simple manner by known processes (compare DE-OS (German Published Specification) No. 2,105,490, DE-OS (German Published Specification) No. 2,201,063 and Org. Synth. 55, 24).

The aroxy-ketones are obtained, for example, by reacting corresponding arylhydroxy compounds with corresponding halogenoketones in the presence of an acid-binding agent and in the presence of a diluent.

Formula (III) provides a general definition of the pyrimidinyl halides also required as starting substances in the process according to the invention. In this formula, Z preferably represents chlorine or bromine.

The pyrimidinyl halides of the formula (III) are generally known compounds of organic chemistry.

Possible diluents in the process according to the invention are all the inert organic solvents. Those organic solvents which have a low melting point, such as, for example, ethers, can preferably be used. Diethyl ether and tetrahydrofuran are particularly preferred here, as well as mixtures of these two solvents.

Preferred alkali metal-organic compounds which can be used in the reaction according to the invention are alkali metal-alkyls, such as, for example, n-butyl-lithium, or alkali metal-aryls, such as, for example, phenyl-lithium.

The reaction temperatures can be varied within a certain range in the process according to the invention. In general, the reaction is carried out at temperatures between $-150°$ C. and $-50°$ C., preferably between $-120°$ C. and $-80°$ C.

The reaction according to the invention is preferably carried out under an inert gas atmosphere, such as, for example, nitrogen or argon.

In carrying out the process according to the invention, the aroxy-ketones of the formula (II) and the pyrimidinyl halides of the formula (III) are in general employed in approximately equimolar amounts. However, it is also possible to use one of the two components in a relatively large excess. The alkali metal-organic compound is in general employed in an excess of 5 to 75 mol %, preferably 10 to 50 mol %. The process can be carried out by a procedure in which the alkali metal-organic compound is first reacted with the pyrimidinyl halide of the formula (III) and the aroxy-ketone of the formula (II) is then added; however, it is also possible to take the aroxy-ketone of the formula (II) and the pyrimidinyl halide of the formula (III) and then to add the alkali metal-organic compound at a low temperature, for example at $-100°$ C. to $-130°$ C.

The epoxy-pyrimidinyl-alkanols of the formula (I) are in general isolated by a procedure in which the alkali metal alkanolate initially formed in the reaction, for example lithium alkanolate, is hydrolyzed with water. Further working-up is effected by customary methods.

All those acids which lead to physiologically acceptable salts can be used for the preparation of acid addition salts of the compounds of the formula (I). Those acids which have already been mentioned as acids preferably to be added on in connection with the description of the substances according to the invention can preferably be used.

The acid addition salts of the compounds of the formula (I) can be prepared in a simple manner by customary salt formation methods. In general, a procedure is followed in which a compound of the formula (I) is dissolved in a suitable inert diluent and an acid is then added. Isolation is effected in a known manner, for example by filtering off the salt and, if appropriate, purifying it by washing with an inert organic solvent.

Salts from those metals which have already been mentioned as metals preferably to be added on in connection with the description of the substances according to the invention can preferably be used for the preparation of metal salt complexes of the compounds of the formula (I). Preferred possible anions of these metal salts are anions of hydrogen halide acids, such as, for example, hydrochloric acid and hydrobromic acid, and furthermore, phosphoric acid, nitric acid and sulphuric acid.

The metal salt complexes of compounds of the formula (I) can be prepared in a simple manner by customary methods. In general, a procedure is followed in which a metal salt is dissolved in alcohol, such as, for example, ethanol, and a compound of the formula (I) is then added. Isolation is likewise effected in a known manner, for example by filtering off the metal salt complex and, if appropriate, purifying it by recrystallization.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention are particularly suitable for inhibiting the longitudinal growth of plants, in particular of cereals, such as, for example, barley, wheat, rye, oats and rice.

The active compounds according to the invention also exhibit a powerful fungicidal and microbicidal action and can therefore be employed for combating undesired fungi and micro-organisms.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds according to the invention, at the concentrations required for combating plant diseases, permits treatment of above-ground parts of plants, of vegetative propagation stock and seeds, and of the soil.

As fungicidal agents, the active compounds according to the invention can be used with particularly good success for combating those fungi which cause powdery mildew diseases; for example for combating Erysiphe species, such as against the powdery mildew of barley or cereal causative organism (*Erysiphe graminis*). They also show particularly good successes against the apple scab causative organism (*Venturi unaequalis*), and against *Pyricularia oryzae* in rice.

It should be particularly emphasised that the active compounds according to the invention not only display a protective action but also have a systemic action. It is thus possible to protect plants from fungal attack if the active compound is fed to the above-ground parts of the plants via the soil and the roots or via the seed. The substances according to the invention also exhibit a good fungicidal action against Fusaria, Septoria, *Cochliobolus sativus* and *Pyrenophora teres* in cereals. The substances according to the invention moreover also have good herbicidal properties.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example, alkylaryl polyglycol ethers, alkylsulphonates, alkyl-sulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabics, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo- and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultralow volume process or to inject the active compound preparation or the active compound itself into the soil. It is also possible to treat the seeds of plants.

When the active compounds according to the invention are used as plant growth regulators, the amounts applied can be varied within a substantial range. In general, 0.001 to 5 kg, preferably 0.005 to 1 kg, of the active compound are employed per hectare of soil surface.

For use of the substances according to the invention as plant growth regulators, the rule is that the growth regulators are applied within a preferred period of time, the exact definition of which depends on the climatic and vegetative circumstances.

When the substaces according to the invention are used as fungicides, the amounts applied can also be varied within a substantial range, depending on the type of application. Thus, in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and use of the active compounds according to the invention can be seen from the following examples.

Preparation Examples

EXAMPLE 1

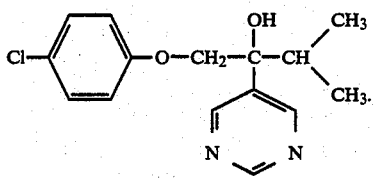

250 ml of a 50% strength solution of n-butyl-lithium in hexane were added dropwise, at −115° C. to −120° C., with stirring, to a solution of 206.7 g (1.3 mols) of 5-bromo-pyrimidine in 2 liters of a mixture consisting of equal parts of absolute diethyl ether and absolute tetrahydrofuran. After the mixture had been subsequently stirred at −115° to 120° C. for one hour, a solution of 282 g (1.3 mols) of 1-(4-chlorophenoxy)-3-methyl-butan-2-one in 500 ml of absolute tetrahydrofuran was added dropwise at the same temperature. The reaction mixture was stirred at −115° C. to −120° C. for a further 2 hours and the cooling bath was then replaced by an acetone/dry ice cooling bath and stirring was continued for 16 hours. A solution of 80.3 g (1.5 mols) of ammonium chloride in a little water was then added dropwise. After the aqueous phase had been removed, the organic phase was washed successively with one portion of half-saturated and two portions of saturated aqueous sodium chloride solution and then dried over sodium sulphate and concentrated by stripping off the solvent under reduced pressure. The residue which remained was dissolved in 1.5 liters of toluene and the solution was extracted successively with 320 ml and then with 40 ml of half-concentrated aqueous hydrochloric acid. The hydrochloric acid extract was then covered with a layer of 1 liter of toluene and rendered basic by slow addition of 45% strength aqueous sodium hydroxide solution, while cooling, and the aqueous phase was separated off and extracted again with toluene. After the solvent had been stripped off under reduced pressure, a light brown oil remained, which gradually crystallized completely. 254 g (66.8% of theory) of 1-(4-chloro-phenoxy)-3-methyl-2-pyrimidin-5-yl)-butan-2-ol were obtained in this manner in the form of a test substance of melting point 77°–78° C. Preparation of the starting substance of the formula

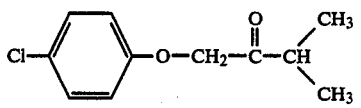

338 g (2.77 mols) of 1-bromo-3-methyl-butan-2-one were rapidly added dropwise to a mixture of 357 g (2.78 mols) of 4-chlorophenol and 483 g (3.5 mols) of potassium carbonate in 2.5 liters of methyl ethyl ketone. The mixture was heated under reflux for 16 hours and then filtered. The filtrate was concentrated by stripping off the solvent under reduced pressure, the residue was taken up in methylene chloride and the organic phase was washed twice with 2N aqueous sodium hydroxide solution, once with water and once with saturated aqueous sodium chloride solution. After drying, the organic phase was concentrated by stripping off the solvent. The residue which remained was distilled under a high vacuum. 435 g (74% of theory) of 1-(4-chlorophenoxy)-3-methyl-butan-2-one were obtained in this manner.

Boiling point = 103°–105° C./0.15 mbar.

The substances according to the invention listed by way of their formulae in the following examples can be prepared by the method described in Example 1.

TABLE 1

$$R-O-CH_2-\underset{\underset{\underset{N \diagup \!\!\!\!\diagdown N}{\|}}{\overset{\overset{OH}{|}}{C}}}{}-CH\overset{CH_3}{\underset{CH_3}{\diagdown}} \quad (I)$$

| Example number | R | melting point [°C.] refractive index [$n_D^{20}$] |
|---|---|---|
| 2 | naphthyl | 96–98 |
| 3 | 2,4-dichlorophenyl | 127–128 |
| 4 | 4-chloro-2-methylphenyl | 117–118 |
| 5 | 4-methylphenyl | 1.5497 |
| 6 | biphenyl | 157–158 |
| 7 | 4-methoxyphenyl | 95–96 |
| 8 | 4-trifluoromethoxyphenyl | 1.5081 |
| 9 | 2,6-dimethylphenyl | 98–99 |

TABLE 1-continued

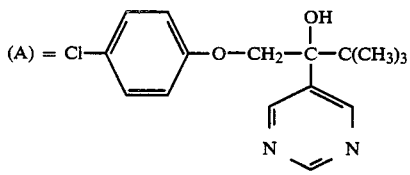

| Example number | R | melting point [°C.] refractive index [n$_D^{20}$] |
|---|---|---|
| 10 | 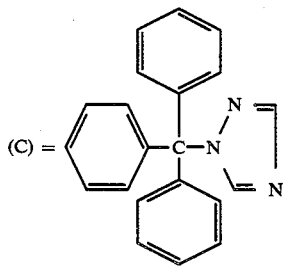 | 87–88 |
| 11 | 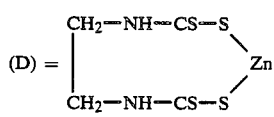 | 93–94 |

The substances shown below were used as comparison components in the use examples which follow:

(A) =

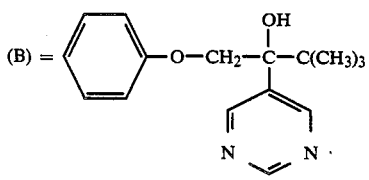

[3,3-Dimethyl-1-(4-chloro-phenoxy)-2-(pyrimidin-5-yl)-butan-2-ol; known from DE-OS (German Published Specification) 2,742,173]

(B) =

[3,3-Dimethyl-1-phenoxy-2-(pyrimidin-5-yl)-butan-2-ol; known from DE-OS (German Published Specification) 2,742,173]

(C) =

(D) =

EXAMPLE A

Inhibition of growth of soy beans

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. In this stage, the plants are sprayed with the preparations of active compound until dripping wet. After 3 weeks, the additional growth is measured on all the plants and the inhibition of growth in percent of the additional growth of the control plants is calculated. 100% inhibition of growth means that growth has stopped and 0% denotes a growth corresponding to that of the control plants.

In this test, compound (1) according to the invention showed a significantly more powerful growth-inhibiting action than comparison substance (A), both at a concentration of 0.05% and at a concentration of 0.0125%.

TABLE A

| | Inhibition of growth of soybeans | |
|---|---|---|
| Active compound | Concentration (in %) | Inhibition of growth (in %) |
| — (control) | — | 0 |
| (A) (known) | 0.05 | 78 |
| | 0.0125 | 65 |
| (1) | 0.05 | 95 |
| | 0.0125 | 88 |
| (3) | 0.05 | 82 |
| (5) | 0.05 | 89 |
| (7) | 0.05 | 89 |
| (8) | 0.05 | 86 |
| (11) | 0.05 | 89 |

EXAMPLE B

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and the inhibition of growth in percent of the additional growth of the control plants is calculated. 100% inhibition of growth means that growth has stopped and 0% denotes a growth corresponding to that of the control plants.

In this test, compound (1) according to the invention showed a significantly more powerful growth-inhibiting action than comparison substance (A), at a concentration of 0.05%. At concentrations lower than 0.05%, growth was no longer inhibited by compound (A), whereas compound (1) according to the invention still exerted a significant effect.

TABLE B

| | Inhibition of growth of barley | |
|---|---|---|
| Active compound | Concentration (in %) | Inhibition of growth (in %) |
| — (control) | — | 0 |
| (A) (known) | 0.05 | 49 |
| | 0.025 | 0 |
| | 0.0125 | 0 |
| (1) | 0.05 | 64 |
| | 0.0125 | 38 |

EXAMPLE C

Puccinia test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, compound (1) according to the invention showed a significantly better action than comparison substance (A), at a concentration of 0.025%.

TABLE C

| | Puccinia test (wheat)/protective | |
|---|---|---|
| Active compound | Active compound concentration in the spray liquor in % by weight | Disease infestation in % of the untreated control |
| known: (A) [4-Cl-C6H4-OCH2-C(OH)(C(CH3)3)-pyrimidinyl] | 0.025 | 72.5 |
| according to the invention: (1) [4-Cl-C6H4-OCH2-C(OH)(CH(CH3)2)-pyrimidinyl] | 0.025 | 25.0 |

EXAMPLE D

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.* sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, compound (1) according to the invention showed a significantly better action than comparison substance (B), at a concentration of 0.00025%.

TABLE D

| | Erysiphe test (barley)/protective | |
|---|---|---|
| Active compound | Active compound concentration in the spray liquor in % by weight | Disease infestation in % of the untreated control |
| known: (B) [C6H5-OCH2-C(OH)(C(CH3)3)-pyrimidinyl] | 0.00025 | 100 |
| according to the invention: (1) [4-Cl-C6H4-OCH2-C(OH)(CH(CH3)2)-pyrimidinyl] | 0.00025 | 48.7 |

EXAMPLE E

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on the plants are inoculated with an aqueous conidia suspension of the apply scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

The active compounds, active compound concentrations and results can be seen from the table which follows.

TABLE E

Venturia test (apple)/protective

| Active compound | Infestation in % at an active compound concentration of | |
|---|---|---|
| | 25 ppm | 10 ppm |
| known: | 82 | |

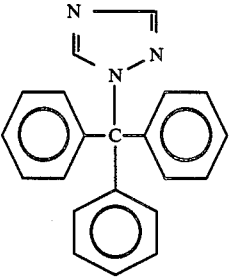

| according to the invention: | 20 | |

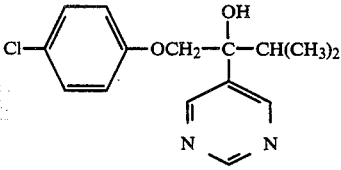

EXAMPLE F

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

The active compounds, active compound concentrations and results can be seen from the table which follows.

TABLE F

Pyricularia test (rice)/protective

| Active compound | Active compound concentration in % | Disease infestation in % of the untreated control |
|---|---|---|
| known: | 0.025 | 75 |

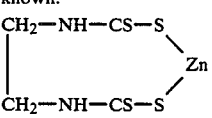

| According to the invention: | 0.025 | 20 |

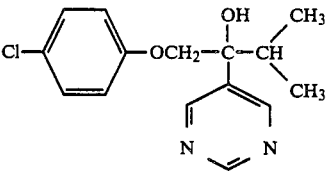

EXAMPLE G

Inhibition of growth of grass (*Festuca pratensis*)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Grass (*Festuca pratensis*) was grown in a greenhouse up to a height in growth of 5 cm. In this stage, the plants were sprayed with the preparations of active compound until dripping wet. After 3 weeks, the additional growth was measured and the inhibition of growth in percent of the additional growth of the control plants was calculated. 100% inhibition of growth meant that growth had stopped and 0% denoted a growth corresponding to that of the control plants.

The active compounds, active compound concentrations and results can be seen from the table which follows:

TABLE G

Inhibition of growth of grass (*Festuca pratensis*)

| Active compound | Active compound concentration in % | Inhibition of growth in % |
|---|---|---|
| — (Control) | — | = 0 |
| (4) | 0.05 | 76 |
| (5) | 0.05 | 66 |
| (8) | 0.05 | 91 |
| (9) | 0.05 | 66 |

EXAMPLE H

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th secondary leaf had unfolded completely. In this stage, the plants were sprayed with the preparation of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

The active compounds, active compound concentrations and results can be seen from the table which follows:

TABLE H

| Active compound | Active compound concentration in % | Inhibition of growth in % |
|---|---|---|
| — (Control) | — | = 0 |
| (3) | 0.05 | 82 |
| (4) | 0.05 | 100 |
| (5) | 0.05 | 76 |
| (7) | 0.05 | 76 |
| (8) | 0.05 | 80 |
| (10) | 0.05 | 100 |
| (11) | 0.05 | 76 |

It is understood that the specification and examples are illustrative but not limitative of the present invention and that other embodiments within the spirit and scope of the invention will suggest themselves to those skilled in the art.

We claim:

1. An aroxy-pyrimidinyl-alkanol of the formula

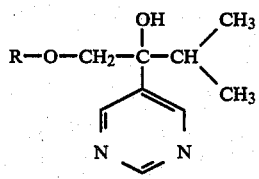

in which R is naphthyl or

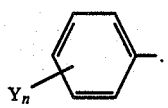

Y each independently is fluorine, chlorine, methyl, methoxy, trifluoromethoxy, or phenyl and n is 0, 1, 2 or 3.

2. A compound according to claim 1, wherein such compound is 1-(4-chloro-phenoxy)-3-methyl-2-(pyrimidin-5-yl)-butan-2-ol of the formula

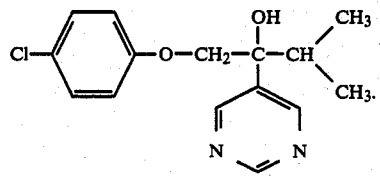

3. A compound according to claim 1, wherein such compound is 1-(4-chloro-2-methyl-phenoxy)-3-methyl-2-(pyrimidin-5-yl)-butan-2-ol of the formula

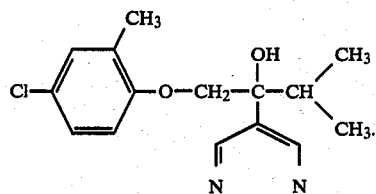

4. A compound according to claim 1, wherein such compound is 1-(4-methyl-phenoxy)-3-methyl-2-(pyrimidin-5-yl)-butan-2-ol of the formula

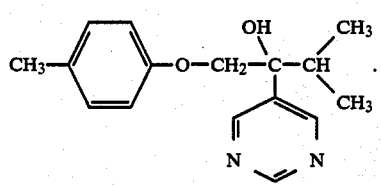

5. A compound according to claim 1, wherein such compound is 1-(4-trifluoromethoxy-phenoxy)-3-methyl-2-(pyrimidin-5-yl)-butan-2-ol of the formula

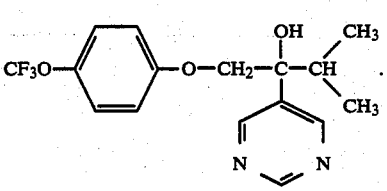

6. A compound according to claim 1, wherein such compound is 1-(2,3-dimethyl-phenoxy)-3-methyl-2-(pyrimidin-5-yl)-butan-2-ol of the formula

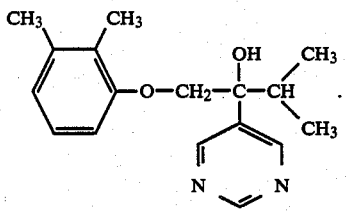

7. A plant growth regulating composition comprising a plant growth regulating effective amount of a compound according to claim 1 in admixture with a diluent.

* * * * *

UNITED STATES PATENT AND TRADEMARK OFFICE
CERTIFICATE OF CORRECTION

PATENT NO. : 4,584,373
DATED : April 22, 1986
INVENTOR(S) : Graham Holmwood, et al.

It is certified that error appears in the above-identified patent and that said Letters Patent is hereby corrected as shown below:

Col. 4, line 47    Delete "epoxy" and substitute --aroxy--

Signed and Sealed this

Sixteenth Day of September 1986

[SEAL]

Attest:

DONALD J. QUIGG

Attesting Officer    Commissioner of Patents and Trademarks